United States Patent [19]
Yagi et al.

[11] Patent Number: 6,007,697
[45] Date of Patent: Dec. 28, 1999

[54] METHOD FOR CLEANING A LIMITING CURRENT TYPE GAS SENSOR

[75] Inventors: Hideaki Yagi; Katsuhiko Horii, both of Aichi, Japan

[73] Assignee: NGK Spark Plug Co., Ltd., Aichi, Japan

[21] Appl. No.: 08/821,283

[22] Filed: Mar. 20, 1997

[30] Foreign Application Priority Data

Mar. 21, 1996 [JP] Japan .................................. 8-093347

[51] Int. Cl.⁶ ................................................. G01N 27/407
[52] U.S. Cl. ........................ 205/788; 204/402; 204/425; 204/426; 205/784
[58] Field of Search .......................... 204/402, 421–429, 204/430; 205/783.5, 784, 784.5, 785, 788

[56] References Cited

U.S. PATENT DOCUMENTS

| | | | |
|---|---|---|---|
| Re. 28,792 | 4/1976 | Ruka et al. | 204/426 |
| 2,805,191 | 9/1957 | Hersch | 204/402 |
| 4,950,378 | 8/1990 | Nagata | 204/402 |
| 5,281,314 | 1/1994 | Yagi et al. | 204/426 |
| 5,348,630 | 9/1994 | Yagi et al. | 204/426 |
| 5,496,461 | 3/1996 | Hotzel et al. | 204/425 |

FOREIGN PATENT DOCUMENTS

| | | |
|---|---|---|
| 3-123849 | 5/1991 | Japan. |
| 4-264250 | 9/1992 | Japan. |
| 2 194 056 | 2/1988 | United Kingdom. |
| 2 195 772 | 4/1988 | United Kingdom. |

*Primary Examiner*—T. Tung
*Attorney, Agent, or Firm*—Morrison & Foerster LLP

[57] ABSTRACT

A sensor cleaning method and a detection apparatus enabling easy and correct measurement for an uninterrupted prolonged time duration of the gas concentration.

The method is based on the value of a limiting current generated on applying a dc voltage across a pair of positive and negative electrodes of a sensor in which the electrodes are formed of a porous material and arranged in intimate contact with the surface of a solid electrolyte substrate exhibiting oxygen ion conductivity and in which pores of the negative electrode are used simultaneously as gas diffusion limiting holes for limiting the amount of diffusion of the gas for measurement. If the limiting current characteristics of sensor versus applied voltage are deteriorated, a voltage opposite to that used during measurement is applied for restoring the characteristics to a normal value.

5 Claims, 8 Drawing Sheets

METHOD FOR CLEANING A LIMITING CURRENT TYPE GAS SENSOR

TECHNICAL FIELD OF THE INVENTION

This invention relates to a method for cleaning a limiting current type gas sensor configured for detecting the concentration of a gas such as oxygen or water vapor from the limiting current value which is based on gas ions migrating in the interior of a solid electrolyte, and a detection apparatus employing the cleaning method.

BACKGROUND

Figure 9:
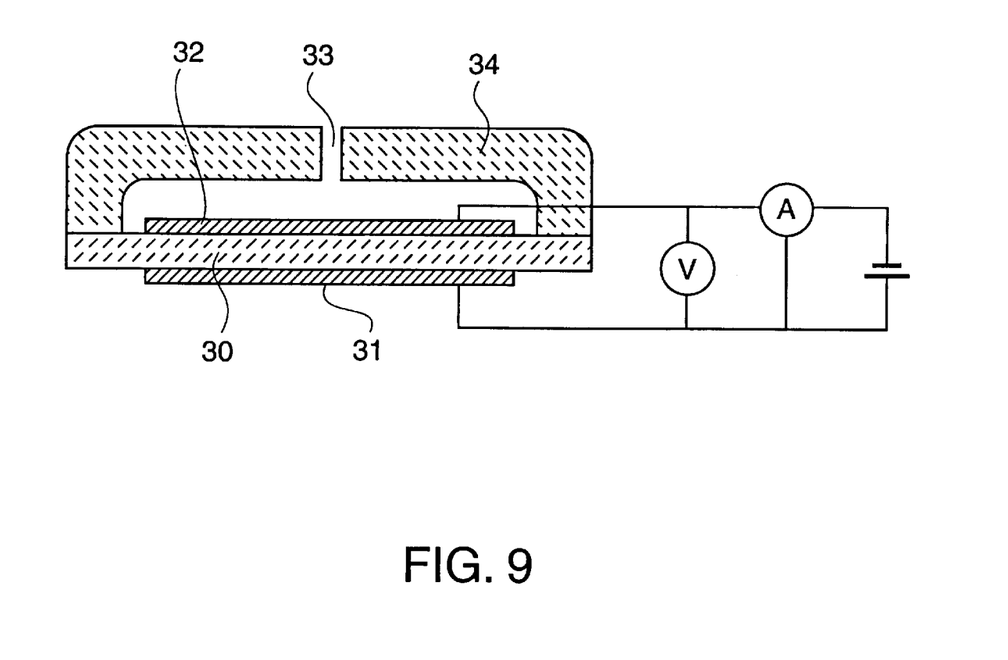
FIG. 9 is a cross-sectional view showing a conventional limiting current type gas sensor.

There has hitherto been known a sensor in which, as shown in FIG. 9, a positive electrode 31 and a negative electrode 32 are provided on the surface of a substrate 30 formed of a solid electrolyte, such as zirconia, and a gas inlet from outside to the negative electrode 32 is formed as a small-sized hole 33 for limiting the gas diffusion towards the negative electrode 32, the gas thus limited being ionized on the surface of the negative electrode 32 so as to be migrated through the inside of the solid electrolyte substrate 30 to produce a limiting current based on which to detect the gas concentration. This sensor is herein termed as a limiting current type gas sensor. There has also been known a sensor of the type in which the negative electrode 32 itself is of a porous structure so that the pores of the negative electrode are used simultaneously as the small-sized hole for limiting the gas diffusion. This structure is superior in that the sensor is of a simple planar structure.

If the apparatus for detecting oxygen or water vapor employing a limiting current type sensor is used for a prolonged period of time, the limiting current characteristics of the sensor versus applied voltage are deteriorated depending on the measurement atmosphere, thus increasing measurement errors. With this in mind, there has been proposed a method in which two sensor elements having different values of the applied voltages at which the limiting current appears are incorporated in one sensor and the current ratio between the two is measured for giving judgment on the degree of deterioration based on the extent of deviation of the measured ratio from the initial value, as disclosed in JP Patent kokai JP-A-4-264250. There has also been proposed a method in which the humidity is found from a ratio of the first limiting current value limited depending on the concentration of oxygen in the measurement atmosphere to the second limiting current value limited depending on the moisture concentration for reducing the error despite sensor deterioration, as disclosed in JP-Patent Kokai JP-A-4-50763 (U.S. Pat. No. 5,281,314).

SUMMARY OF THE DISCLOSURE

According to the investigation toward the present invention, the following problems were encountered.

With the method employing two sensor elements, as disclosed in JP Patent kokai JP-A-4-264250, the sensor becomes complicated in structure. In addition, this method simply permits the deterioration of the sensor to be identified, while correct continuous measurement cannot be achieved. On the other hand, with the method employing the ratio of the two limiting current values, only intermittent measurement can be achieved since the voltage to be applied to the sensor needs to be switched over between an applied voltage at which the first limiting value is developed and another applied voltage at which the second limiting value is developed.

It is therefore an object of the present invention to provide a novel sensor cleaning method and a novel detection apparatus which render it possible to measure the gas concentration easily and correctly for a prolonged non-interrupted time duration, particularly, using a simplified planar type limiting current type gas sensor, more particularly those in which a negative electrode is used simultaneously as a gas diffusion limiting hole.

Still further objects will become apparent from the entire disclosure.

For accomplishing the above object, the present invention provides a method for cleaning the limiting current type gas sensor. The cleaning method is characterized in that if limiting current characteristics of the sensor versus the applied voltage are deteriorated, a voltage opposite to that used during measurement is applied for restoring the characteristics to a normal value. The cleaning method is generally used in a method for measuring the concentration of a gas based on limiting current value generated on applying a dc voltage across a pair of positive and negative electrodes of a sensor in which the electrodes are formed of a porous material and arranged in intimate contact with the surface of a solid electrolyte substrate exhibiting oxygen ion conductivity. In the sensor, typically, pores of the negative electrode are used simultaneously as a gas diffusion limiting hole for limiting the amount of diffusion of the gas for measurement.

The present invention also provides an apparatus for measuring the concentration of a gas. The apparatus comprises a sensor in which a pair of positive and negative electrodes are formed of a porous material and arranged in intimate contact with the surface of a solid electrolyte substrate exhibiting oxygen ion conductivity. Typically, pores of the negative electrode are used simultaneously as a gas diffusion limiting hole for limiting the amount of diffusion of the gas for measurement. The apparatus further comprises: a voltage switching circuit for switching over the voltage applied across the electrodes to a voltage for measurement or to a cleaning voltage of an opposite polarity to that of the voltage for measurement, a linear circuit for converting an output of the sensor during the time of application of the voltage for measurement across the electrodes to a partial pressure signal of the gas under measurement, and a holding circuit for holding the partial pressure signal outputted by the linear circuit immediately before application of the cleaning voltage for a period of time during which the cleaning voltage is applied across the electrodes.

Although the reason of deterioration in the characteristics on prolonged use of the limiting current type gas sensor is not clear, it may be presumed that since the gas in the atmosphere for measurement is inspired at all times via the negative electrode, particularly, when operating as the gas diffusion limiting hole, ingredients other than the gas for measurement in the atmosphere are accumulated on the negative electrode surface or on the interface between the negative electrode and the solid electrolyte substrate to cause changes in the limiting amount of the gas diffused within the negative electrode.

In the present invention, the voltage opposite to that for the normal operation is applied across the electrodes for realizing an opposite operation to that during measurement, that is for capturing oxygen from the positive electrode in the course of measurement, migrating the oxygen ions to the negative electrode in the course of measurement through the solid electrolyte substrate and releasing the oxygen ions from the negative electrode side. This removes pollution (deterioration) on the interface between the solid electrolyte substrate and the electrode for restoring the limiting current value to the initial value. This also serves to remove the pollution produced on the surface of the negative electrode, if any. Moreover, in the conventional current limiting type gas sensor, the gas diffusion limiting hole is a large-sized hole bored by machining, so that the limiting current value is a large value on the order of milliamperes, whereas, in the sensor of an embodiment of the present invention, the negative electrode is formed of a porous material and is used simultaneously as the gas diffusion limiting hole, so that the limiting current value is a small value of one-tenth of the conventional value. Thus, in distinction from the conventional sensor which cannot be operated unless the temperature of the solid electrolyte substrate is raised to approximately 700° C., the sensor of the present invention operates at approximately 500° C. The result is that the decomposition of the solid electrolyte, that is blackening, is less likely to occur than with the conventional sensor, so that the absolute value of the cleaning voltage can be set to a higher value thus assuring efficient cleaning.

The gas concentration cannot be measured during application of the reverse voltage for cleaning. However, with the detection apparatus of the present invention, the partial pressure of the gas under measurement, outputted by the linear circuit immediately before application of the cleaning voltage, is held by the holding circuit during the period of time during which the cleaning voltage is applied across the electrodes, so that, unless the atmosphere is changed acutely, there is no remarkable error between the actual gas concentration and the displayed gas concentration.

PREFERRED EMBODIMENTS OF THE INVENTION

If the gas being measured is water vapor, the limiting current type gas sensor operates as a humidity sensor. It suffices if the voltage applied for restoring the above characteristics to the normal value is set so as to be smaller than an upper limit of the applied voltage used for water vapor measurement. If the absolute value of the applied voltage for cleaning is excessive, the reaction of $ZrO_2 \rightarrow Zr + O_2$ occurs to produce so-called blackening which is embrittlement of the zirconia surface to present a black color. However, since the sensor of the present invention operates at a temperature of approximately 500° C., as stated previously, the upper limit of the applied voltage for water vapor measurement is of a rather high value. Therefore, the applied voltage for cleaning can be set to a rather high value, thereby assuring a high cleaning efficiency.

Cleaning can be achieved automatically if there is provided a timer circuit for setting the interval of applying the voltage for measurement and the voltage for cleaning and instructing the set interval to a voltage switching circuit and to the holding circuit.

The cleaning method can be advantageously applied to oxygen sensors, moisture sensors and the like gas sensors, particularly for the moisture sensors. In the moisture sensors there is a type in which both (a pair of) negative and positive electrodes are disposed on one surface of a substrate plate. In this type of the sensor, or in a sensor in which the measuring current is very small, e.g., about 200 $\mu$A or less, particularly about 100 $\mu$A or less, more particularly several/a few tens (50, 30 or 20) of microamperes or less, the deterioration is likely to occur.

The gas (or moisture) sensors are generally operated in various measuring principles or methods:

(1) The gas concentration is determined by calculating from a directly measured value $I_{L2}$ which is limited according to the gas (e.g., moisture) concentration to be measured.

(2) The gas concentration is determined by ratio $I_{L2}/I_{L1}$ in which $I_{L1}$ represents the first limiting current value limited depending on the oxygen concentration, with $I_{L2}$ representing the second limiting current value limited depending on gas (e.g., moisture) concentration. This method is typically disclosed in U.S. Pat. No. 5,281,314 and the entire disclosure thereof is incorporated herein by reference.

(3) The gas concentration is determined by a difference between $I_{L2}$ and $I_{L1}$, e.g., $(I_{L2}-I_{L1})$.

(4) The gas concentration is determined by a difference from an inflection current $I_m$ which lies between $I_{L1}$ or $I_{L2}$, i.e., $(I^{L2}-I_m)$ or $(I_{L1}-I_m)$.

This method is typically disclosed in U.S. Pat. No. 5,348,630 and the entire disclosure thereof is incorporated herein by reference.

As for the solid electrolyte, zirconia based solid electrolyte is preferred. For measuring the moisture, stabilized zirconia (generally 7 to 15 mol % stabilizer, typically of $Y_2O_3$) is preferred based on the stability against humidity/water. Although the partially stabilized zirconia (e.g., 2–6 mol % stabilizer, typically of $Y_2O_3$) is preferred, even the fully stabilized zirconia (e.g., using MgO etc. as a stabilizer) the deterioration during a prolonged period of time cannot be avoided. Thus the inventive cleaning is of high importance substantially for every kind of the gas sensor, particularly, the moisture sensor.

EXAMPLES

Figure 1:
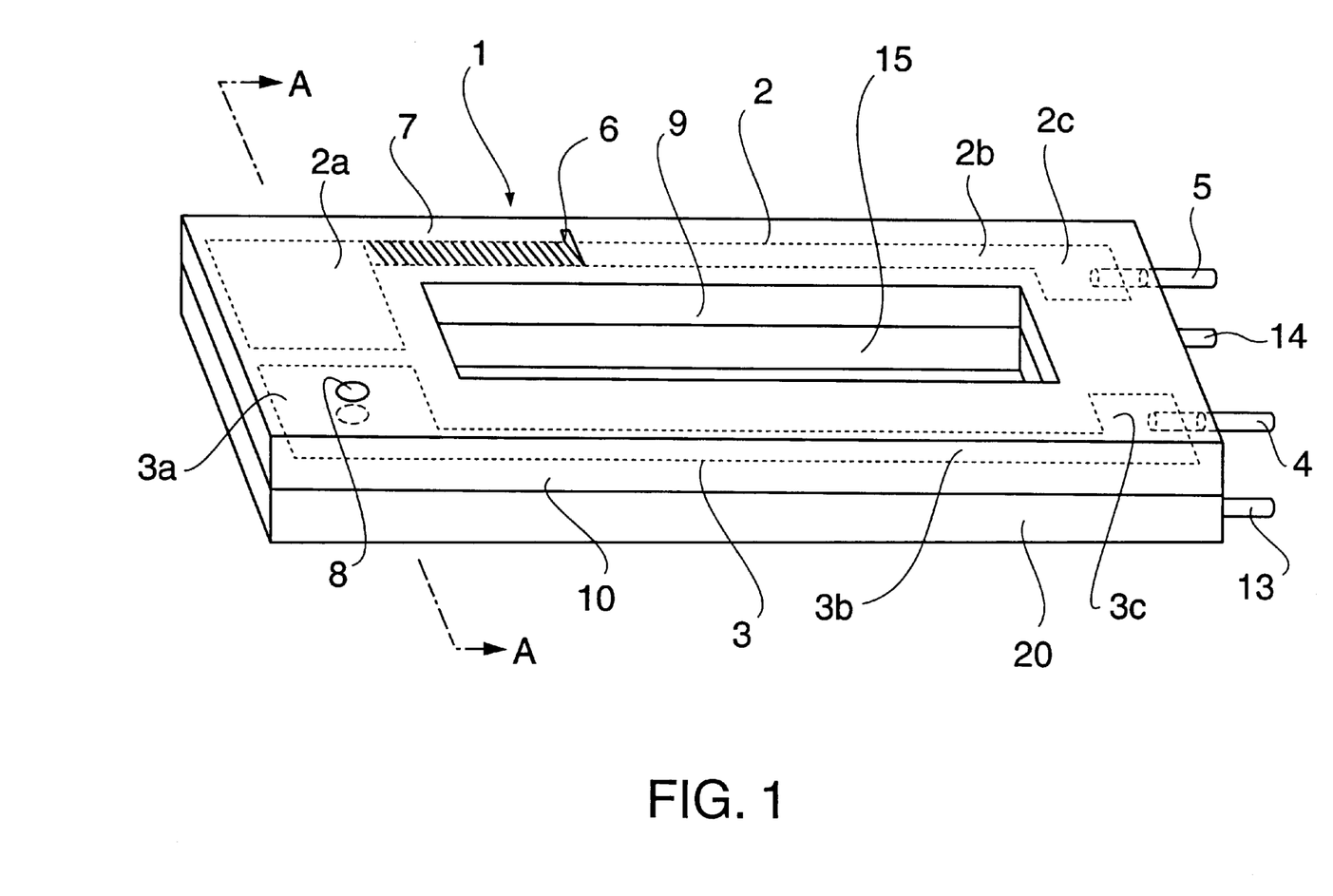
FIG. 1 is a perspective view showing a limiting current type gas sensor employed in a gas detection apparatus according to an embodiment of the present invention.
Figure 2:
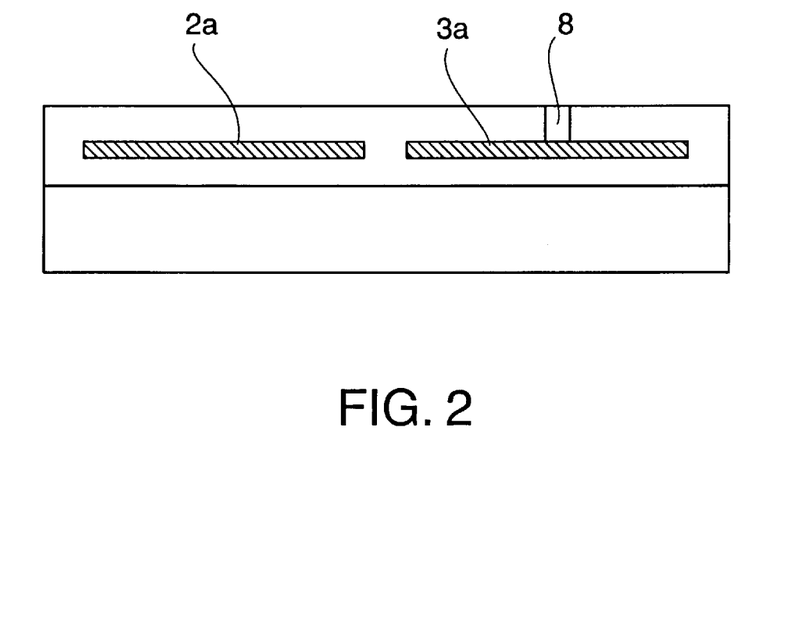
FIG. 2 is a cross-sectional view along line A—A of FIG. 1.
Figure 3:
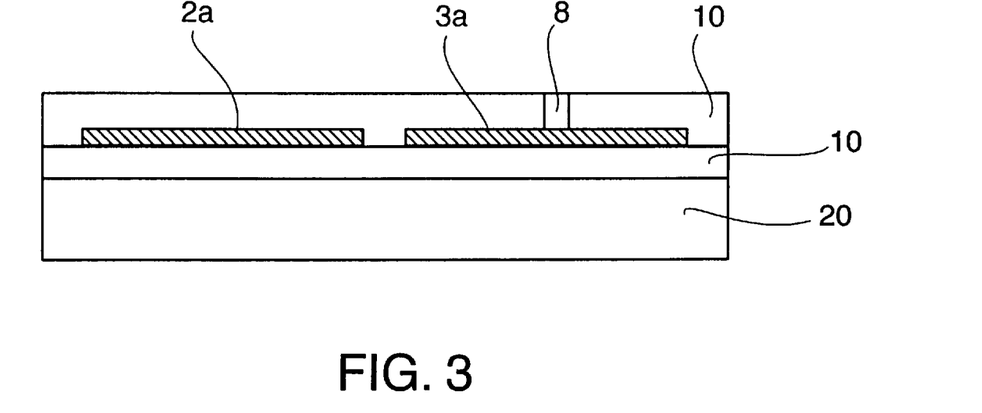
FIG. 3 is a cross-sectional view showing a modification of FIG. 2.
Figure 4:
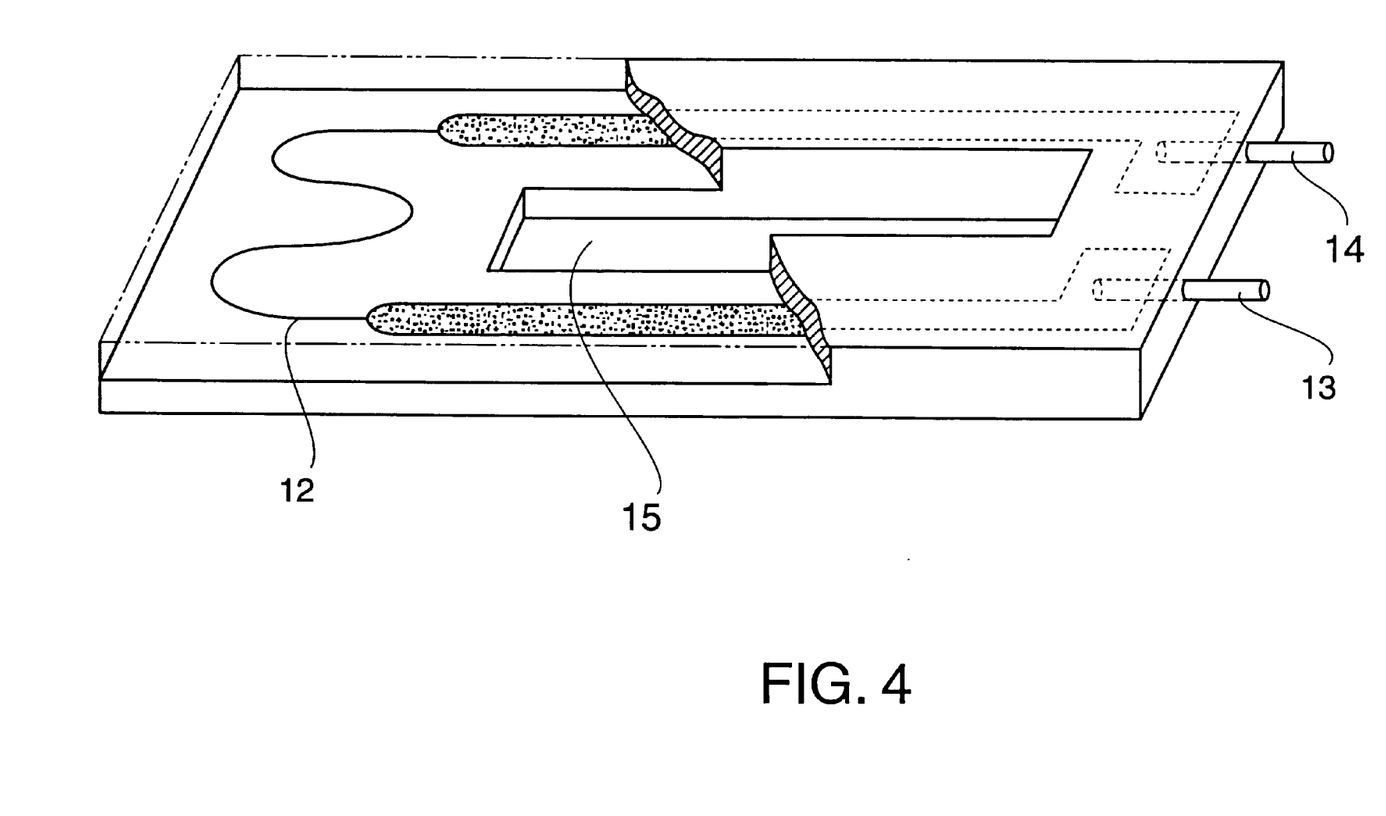
FIG. 4 is a perspective view showing a ceramic heater used in the limiting current type gas sensor, with a portion thereof being removed.

Referring to the drawings, preferred embodiments of the cleaning method for the limiting current type gas sensor (referred to hereinafter simply as 'sensor') and the gas concentration detection apparatus will be hereinafter explained. FIG. 1 is a perspective view showing a limiting current type gas sensor pertaining to a preferred embodiment, FIG. 2 is a cross-sectional view taken along line A—A in FIG. 1, FIG. 3 is a cross-sectional view showing a modification of FIG. 2 and FIG. 4 is a perspective view showing a ceramic heater used in the sensor of FIG. 1, with a portion thereof being removed.

A sensor 1 is made up of a plate-shaped ceramic heater 20, a stabilized zirconia substrate 10, which is a solid electrolyte plate exhibiting oxygen ion conductivity, provided with a major surface of the heater 20, a positive electrode 3 and a negative electrode 2, embedded to be disposed side-by-side within the stabilized zirconia substrate 10, and a gas outlet hole 8.

The stabilized zirconia substrate 10 is a solid electrolyte, which is formed of zirconium oxide admixed with yttrium oxide as a stabilizer in a state of solid solution. In the present embodiment, the zirconium substrate 10 is 0.3 mm in thickness, 5 mm in length and 23 mm in width, and has a center air conduction through-hole 9 extending in the direction of thickness. The ceramic heater 20 and the stabilized zirconia substrate 10 are of the same shape in plan view except a gas outlet 8, and an air conduction hole 15 in register with the air conduction through-hole 9 is formed in the ceramic heater 20.

The positive electrode 3 and the negative electrode 2 are porous platinum layers, with a thickness of tens of micrometers, and are made up of electrode portions 3a, 2a, each having a side measuring approximately 2 mm, elongated leads 3b, 2b and lead out (contact) portions 3c, 2c, respectively. A platinum layer is branched at a mid portion of the lead portions 2b and led to a lateral side of the stabilized zirconia substrate 10 for forming a gas inlet 6. A portion of the length of the lead 2b lying between the gas inlet 6 and the electrode 2a operates as a gas diffusion limiter 7.

The gas outlet 8 is a hole formed in the stabilized zirconia substrate 10 in register with the electrode 3a and operates for establishing communication between the electrode 3a and the outside. The gas outlet 8 may be of any arbitrary shape or size provided that the electrode 3a is in communication with the outside.

The method for producing the sensor 1 will now be explained.

For producing the ceramic heater 20, a heater pattern 12 is printed with a platinum paste on the upper surface of a green sheet, containing 96 wt % of alumina in inorganic ingredients thereof and in which a hole which becomes the air conduction hole 15 after firing is formed. On an end portion of the green sheet are placed platinum terminals 13, 14, and another green sheet of the same structure is placed thereon. The resulting assembly is then fired as one to form a unified ceramic heater 20 (FIG. 4).

In another green sheet, containing a starting material for a solid electrolyte composed of 92 mol % of zirconia and 8 mol % of yttria, a hole which becomes the air conduction hole 9 after firing, is formed. A pair of platinum pastes, which become a positive electrode 3 and a negative electrode 2 after firing, are printed on the green sheet, and platinum terminals 4, 5 are placed on the end of the resulting assembly. A further green sheet of the similar type then is laminated thereon, and the resulting assembly is fired as one at approximately 1500° C. resulting in a sensor element made up of the stabilized zirconia substrate 10, negative and positive electrodes 2, 3 and the platinum terminals 4, 5. After firing, the two green sheets become a unified (solid) zirconia substrate 10, as shown in FIG. 2, such that, on observation of the cross-section after firing, the sheets become hardly distinguishable from each other. The green sheet, on which the platinum pastes are printed, need to be composed mainly of zirconia, hafnia or the like as a solid electrolyte. However, the green sheet, which is laminated thereon, need not be formed of zirconia, but may be formed of, for example, mainly alumina, provided that it can hermetically seal the platinum electrodes therein. In such case, observation of the cross-section indicates a boundary line left between the two sheets, as indicated at 10 in FIG. 3.

The sensor element is secured to the surface of the ceramic heater 20 at approximately 800° C., using a seal glass or the like, to form a sensor 1.

The operation of the sensor 1 is now explained.

Figure 5:
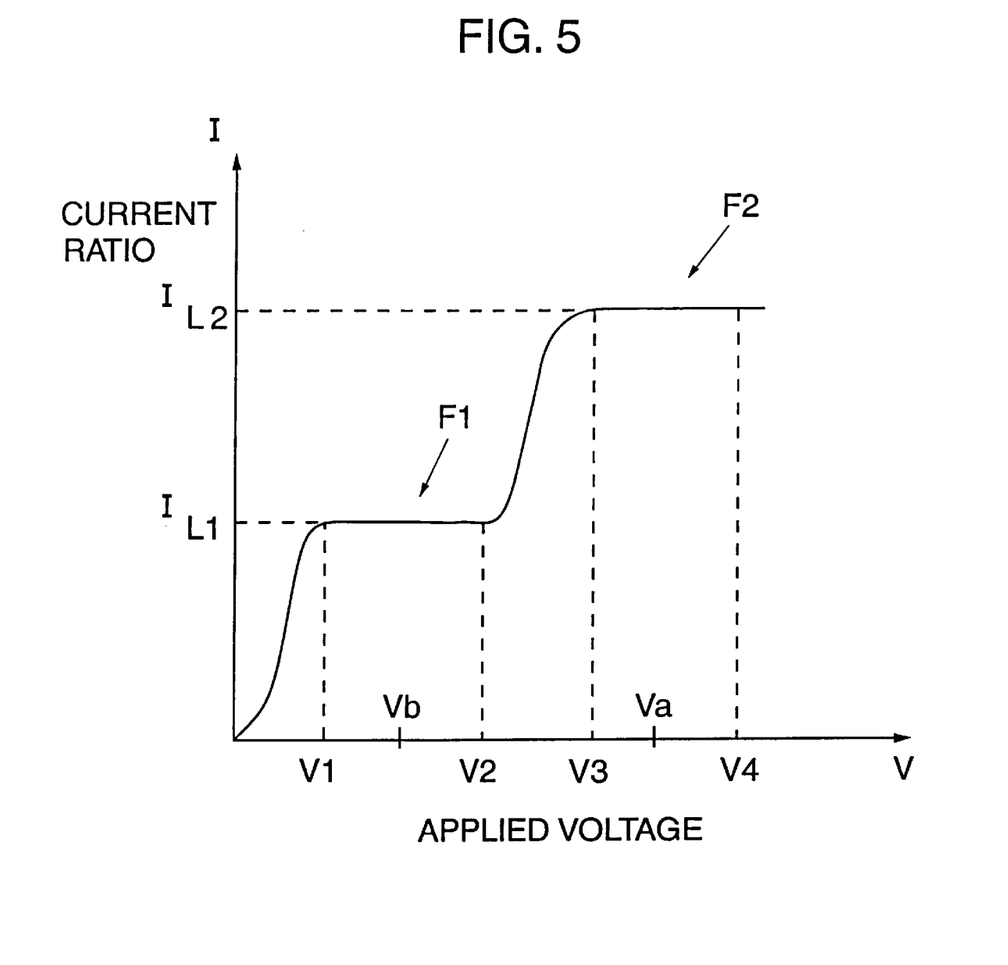
FIG. 5 is a graph showing characteristics of the applied voltage for the limiting current type gas sensor and the current flowing in the sensor when the sensor is placed in a gas for measurement containing oxygen and moisture.

The sensor 1 is placed in a gas for measurement and the current is supplied to the ceramic heater 20 so that the temperature at the electrode portions 2a, 3a will become 500° C., whereupon voltage V is applied across the positive electrode 3 and the negative electrode 2. At this time, oxygen in the electrode portion 2a of the negative electrode 2 is ionized to oxygen ions, with oxygen in the gas for measurement being transported from the negative electrode 2 towards the positive electrode 3 responsive to the applied voltage V. The portion of the negative electrode 2 in the stabilized zirconia substrate 10 lying in the vicinity of the electrode portion 2a is only locally heated, while the portion of the negative electrode 2 provided with the gas diffusion limiter 7 is not heated so sufficiently as to exhibit oxygen ion conductivity. Thus, oxygen is diffused from the gas inlet 6 through the gas diffusion limiter 7 to the interior of the electrode portion 2a without being conducted through the stabilized zirconia substrate 10. At this time, current I flowing across the positive electrode 3 and the negative electrode 2 undergoes transitions as shown in FIG. 5.

For the applied voltage V in a range from V1 t V2, the amount of oxygen diffused into the interior of the electrode portion 2a is controlled by the gas diffusion limiter 7 of the negative electrode 2 and limited responsive to the oxygen concentration in the gas for measurement. Thus, the current value is correspondingly limited to a diffusion limiting current value $I_{L1}$ to give a first planar portion F1. If the applied voltage V becomes higher than the voltage value V2 corresponding to the diffusion limiting current value $I^{L1}$ (usually 1.2 V or higher), the water vapor in the measurement gas is electrically decomposed, and the oxygen ions yielded as a result of the decomposition is pumped from the negative electrode portion 2a to the positive electrode portion 3a, so that the water vapor also is diffused from the gas inlet 6 into the negative electrode portion 2a, and hence the current value is increased responsive to the amount of the diffused water vapor.

If the applied voltage V is increased further to voltage values V3 to V4, the current value is increased further responsive to the water vapor concentration. However, the amount of diffusion of the water vapor is limited by the gas diffusion limiter 7 of the negative electrode 2 and the current value is correspondingly limited, so that the current value becomes a diffused current value $I_{L2}$ corresponding to the water vapor concentration to present a second planar portion F2.

Figure 6:
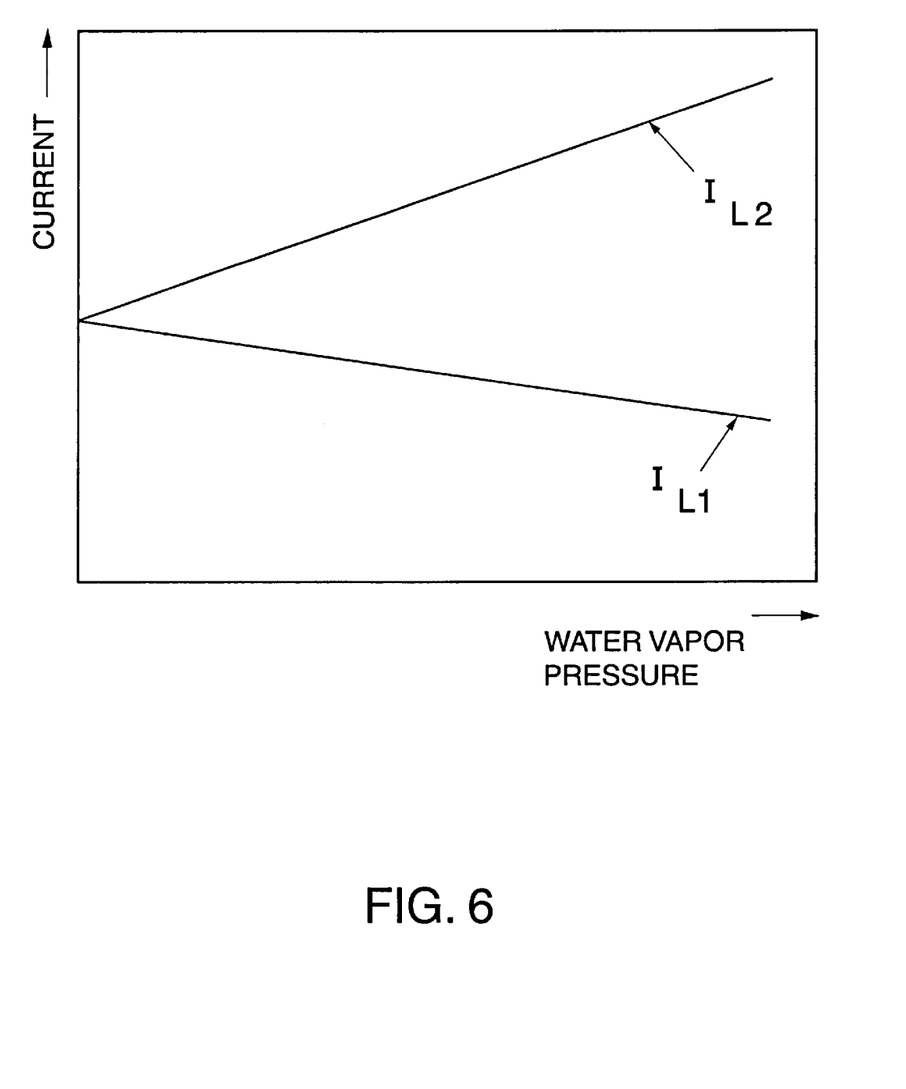
FIG. 6 is a graph showing characteristics of the water vapor concentration and the first and second diffusion limiting currents in case of employing the limiting current type gas sensor.

For a constant oxygen concentration (21% in atmosphere), the two current values $I_{L1}$, $I^{L2}$ can present linear transitions in the right downward direction and in the right upward direction, respectively, as shown in FIG. 6. In any case, the gas diffusion limiter 7 in the present embodiment is not a through-hole that can be observed macroscopically, as in the case of a conventional gas sensor, but is a microscopic pore formed by firing a platinum paste. Thus the current value is as low as tens of microamperes.

Figure 7:
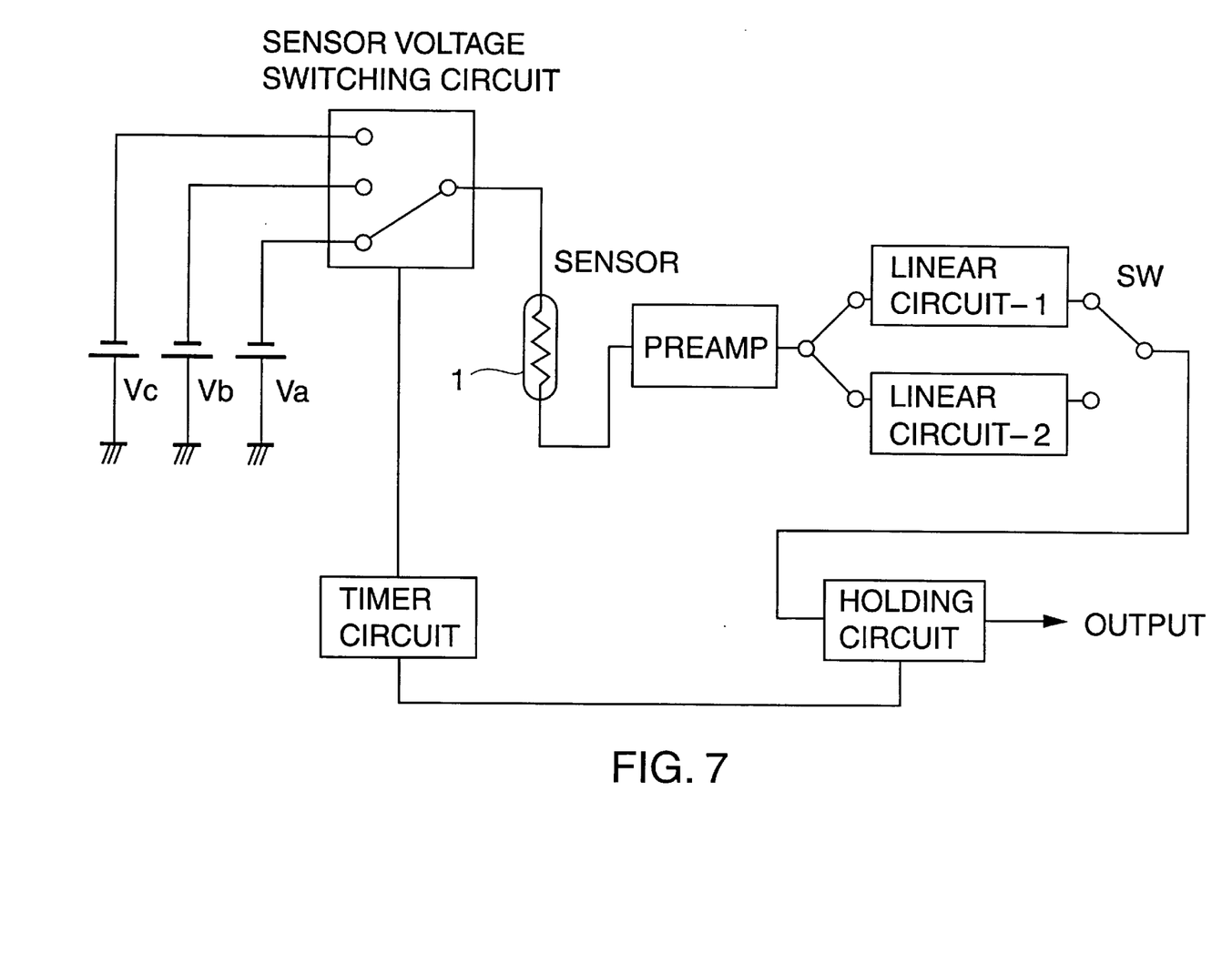
FIG. 7 shows a circuit structure of a gas detection apparatus according to an embodiment of the present invention.

Using this sensor, an output is taken out by a detection apparatus having the circuit structure as shown in FIG. 7. The detection apparatus includes a sensor 1, and a voltage switching circuit for switching the voltage applied across the electrodes 2, 3 of the sensor 1 between a voltage for measuring the water vapor concentration Va, a voltage for measuring the oxygen concentration Vb and a cleaning voltage having the polarity reversed from that of the voltages Va or Vb. The detection apparatus also includes a preamplifier for amplifying a current signal outputted by the sensor 1 for conversion to a voltage signal, and a linear circuit-1 for converting the output of the sensor 1 during application of the voltage Va across the electrodes to a signal of water vapor partial pressure. The detection apparatus also includes a linear circuit-2 for converting the output of the sensor 1 during application of the voltage Vb across the electrodes to a signal of an oxygen partial pressure, and a holding circuit for holding the partial pressures outputted by the linear circuits-1 or 2 immediately before application of Vc during the time of application of Vc across the electrodes. The detection apparatus further includes a timer circuit for setting the time intervals of applying the measurement voltages va, Vb and the cleaning voltage Vc and instructing the time intervals to the voltage switching circuit and to the holding circuit.

If the sensor application voltage V is set at a voltage range from V1 to V2, which gives diffusion limiting currents $I_{L1}$, $I_{L2}$, corresponding to the oxygen concentration, an output becomes proportionate to the oxygen concentration, thus enabling detection of the oxygen concentration. Therefore, the voltages are set so that V1<Vb<V2 is established.

On the other hand, if the sensor applied voltage V is set to a voltage range from V3 to V4, which gives the diffusion limiting current $I_{L2}$ corresponding to the water vapor concentration, an output is proportionate to the water vapor concentration to render it possible to detect the water vapor concentration. Therefore, Va is set for satisfying the relation V3<Va<V4.

The linear circuit-1 corresponds to a straight line $I_{L2}$ of FIG. 6 and converts an output of the preamplifier to a signal of corresponding water vapor pressure (water vapor concentration), while the linear circuit-2 corresponds to a straight line $I_{L1}$ of FIG. 6.

The case in which the sensor characteristics are deteriorated due to prolonged use of the sensor will now be explained. If the sensor is used for a prolonged period of time, the sensor electrode surface or the interface between the solid electrolyte substrate and the electrode becomes polluted such that the voltage-current characteristics undergo transitions as indicated by a dotted chain line in FIG. 8, with the currents $I_{L1}$, $I_{L2}$ being lowered to $I_{L1}$, $I_{L2}$, respectively. If the contamination proceeds further, the voltage-current characteristics undergo transitions as indicated by a double-dotted chain line in FIG. 8 such that the planar portions F1, F2 disappear resulting in significant error in the output.

Figure 8:
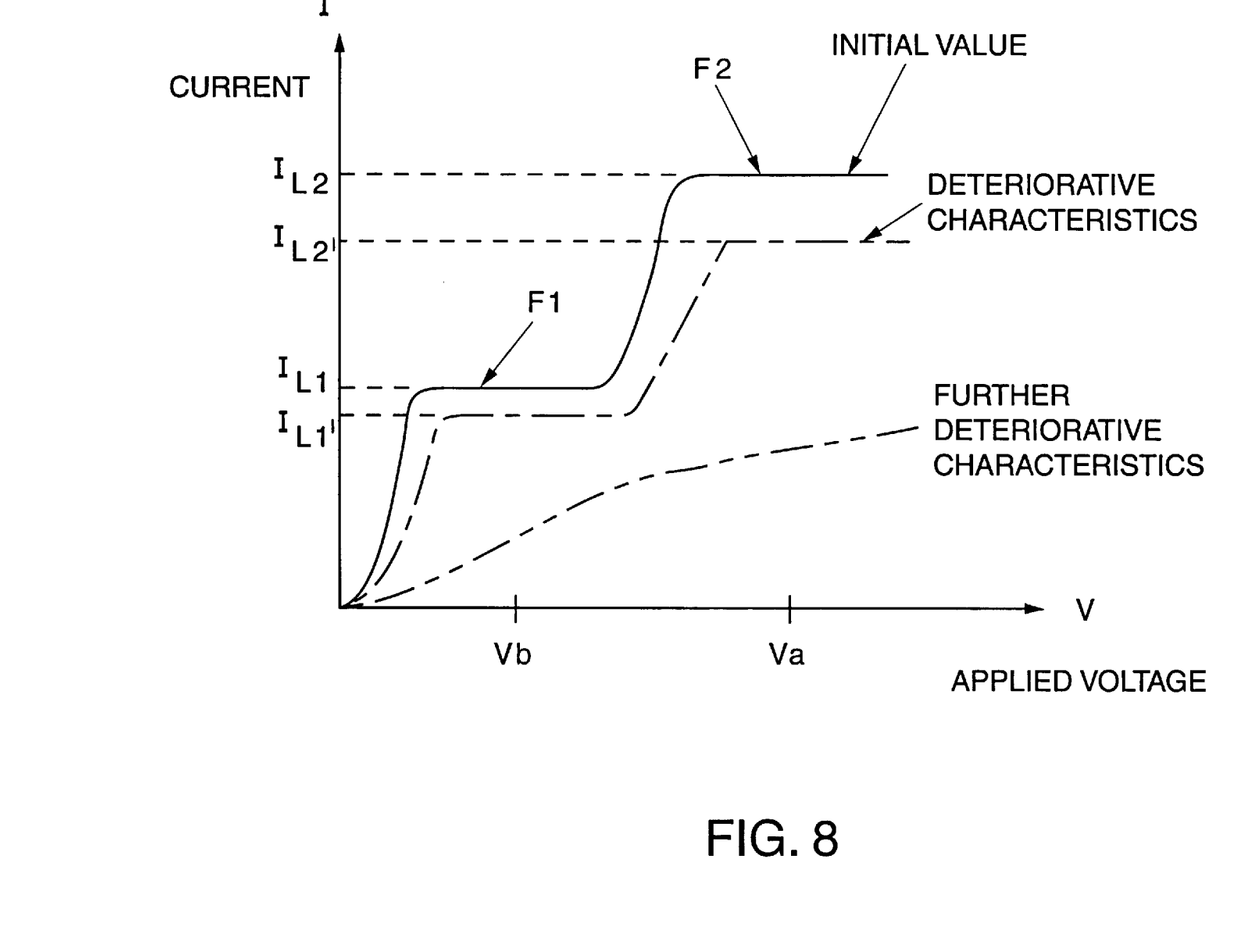
FIG. 8 is a graph showing the applied voltage and the state of deterioration of characteristics of the limiting current flowing in the sensor when the current limiting type gas sensor is placed in the gas for measurement containing oxygen and moisture.

If the voltage Vc is applied to the sensor electrodes in a direction opposite to that during normal measurement, that is so that the negative and positive voltages are applied to the positive and negative electrodes, respectively, the sensor characteristic can be restored to the initial values. Therefore, it becomes possible to measure the oxygen or water vapor concentration again correctly.

It may be presumed that, by applying a voltage in a direction opposite to that during measurement, oxygen is captured from the positive electrode during measurement to migrate oxygen ions through the solid electrode substrate to the negative electrode during measurement to emit the oxygen ions from the negative electrode for removing pollution produced on the negative electrode surface or on the interface between the solid electrolyte substrate and the electrode to reset the sensor characteristics to the initial values.

It suffices if the opposite voltage Vc is opposite to that used during usual measurement and has a value not higher than V4. The proper value of the opposite voltage is from V1 to V4, that is between 0.5 to 2.5 V. Since a lower electrode temperature of 500° C. may be used in the gas sensor of the present invention, a higher voltage than the voltage used for the conventional gas sensor may be applied thus assuring a higher cleaning efficiency. The application time may be selected to be within tens of seconds to tens of minutes depending on the degree of sensor deterioration.

Since the timer circuit is annexed, the reverse voltage Vc can be applied at a pre-set time interval depending on the degree of the sensor deterioration for measuring the oxygen concentration or the water vapor concentration with high precision for a prolonged time.

The subject matter of the claims will be defined by the appended claims. However, it is not excluded to further enlarge, narrow or modify the claims within the entire disclosure.

Also it should be noted that any modification may be done without departing from the scope as defined by the claims based on the gist of the invention herein disclosed in the entire application.

What is claimed is:

1. A method for measuring a concentration of water vapor in a gas comprising:

providing a sensor that has positive and negative porous electrodes arranged in contact with a surface of a solid electrolyte substrate exhibiting oxygen-ion conductivity, measuring the concentration of said water vapor based on a limiting current of less than about 200 $\mu$A generated on applying a dc voltage across said electrodes, said limiting current being responsive to the concentration of said water vapor and restoring a characteristic of said limiting current to a normal value by applying a voltage opposite to and smaller than said dc voltage across said electrodes when said characteristic is deteriorated.

2. The method of claim 1, wherein pores of the negative electrode are used as gas diffusion limiting holes for limiting the diffusion of said gas and said negative electrode is not directly exposed to said gas.

3. The method of claim 2, wherein said negative electrode is covered with a solid layer and communicates with said gas via a diffusion limiter formed as a porous lead connecting said negative electrode to said gas.

4. The method of claim 1, wherein said limiting current value is 100 $\mu$A or less.

5. The method of claim 1, wherein said limiting current value is 50 $\mu$A or less.

* * * * *